United States Patent
Jackson et al.

(10) Patent No.: US 8,463,398 B2
(45) Date of Patent: Jun. 11, 2013

(54) ELECTRODE SURFACE MODIFICATION FOR IMPARTING CURRENT DENSITY DIRECTIONALITY IN LEAD ELECTRODES

(75) Inventors: Timothy R. Jackson, Minneapolis, MN (US); Joseph Schroeder, Eden Prairie, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 12/946,214

(22) Filed: Nov. 15, 2010

(65) Prior Publication Data

US 2011/0160821 A1  Jun. 30, 2011

Related U.S. Application Data

(60) Provisional application No. 61/291,157, filed on Dec. 30, 2009.

(51) Int. Cl.
*A61B 5/05* (2006.01)
*A61B 5/04* (2006.01)
*A61N 1/00* (2006.01)

(52) U.S. Cl.
USPC ........... 607/115; 600/345; 600/372; 600/373; 600/374; 600/375; 607/2; 607/116

(58) Field of Classification Search
USPC ............... 600/345, 372–375; 607/2, 115, 116
See application file for complete search history.

(56) References Cited

U.S. PATENT DOCUMENTS

| | | | |
|---|---|---|---|
| 4,962,767 A | 10/1990 | Brownlee | |
| 4,972,847 A | 11/1990 | Dutcher et al. | |
| 4,979,517 A | 12/1990 | Grossman et al. | |
| 5,042,463 A | 8/1991 | Lekholm | |
| 5,578,067 A | 11/1996 | Ekwall et al. | |
| 6,119,044 A * | 9/2000 | Kuzma | 607/137 |
| 6,240,322 B1 | 5/2001 | Peterfeso et al. | |
| 6,430,425 B1 | 8/2002 | Bisping | |
| 2003/0139794 A1 | 7/2003 | Jenney et al. | |
| 2005/0049665 A1 | 3/2005 | Brabec et al. | |

(Continued)

FOREIGN PATENT DOCUMENTS

| | | |
|---|---|---|
| WO | WO2007001218 A1 | 1/2007 |
| WO | WO2007115198 A2 | 10/2007 |

OTHER PUBLICATIONS

Anderson, Sara E. et al., "Microanatomy of Human Left Ventricular Coronary Veins", The Anatomical Record, vol. 292, pp. 23-28, 2009.

(Continued)

*Primary Examiner* — Niketa Patel
*Assistant Examiner* — Lindsey G Hankins
(74) *Attorney, Agent, or Firm* — Faegre Baker Daniels LLP (57) ABSTRACT

An implantable medical lead having a modified electrode surface for imparting current density directionality within an electrode is disclosed. An implantable medical lead includes a lead body having a proximal section and a distal section having a pre-biased shape configured to secure the lead to an inner wall of a blood vessel. An electrode coupled to the distal section of the lead body includes a number of surface features on an inactive portion of the electrode that impart a current density directionality towards an active portion of the electrode that contacts the inner wall of the vessel. Methods for imparting current density directionality within an implantable lead electrode are also disclosed.

20 Claims, 6 Drawing Sheets

U.S. PATENT DOCUMENTS

| | | |
|---|---|---|
| 2005/0060885 A1 | 3/2005 | Johnson et al. |
| 2005/0182464 A1 | 8/2005 | Schulte et al. |
| 2005/0222660 A1 | 10/2005 | McAuliffe et al. |
| 2006/0009829 A1 | 1/2006 | Aron et al. |
| 2006/0121080 A1 | 6/2006 | Lye et al. |
| 2006/0122681 A1 | 6/2006 | Kroll et al. |
| 2007/0067008 A1 | 3/2007 | Scheiner et al. |
| 2007/0142890 A1 | 6/2007 | Zarembo et al. |
| 2008/0057784 A1 | 3/2008 | Zarembo et al. |
| 2009/0248126 A1 | 10/2009 | Nippoldt et al. |
| 2011/0156306 A1 | 6/2011 | Morris et al. |
| 2011/0160822 A1 | 6/2011 | Jackson et al. |
| 2011/0160823 A1 | 6/2011 | De Kock et al. |

OTHER PUBLICATIONS

United States Statutory Invention Registration No. H1905, to Michael R. S. Hill, published Oct. 3, 2000.

International Search Report and Written Opinion issued in PCT/US2010/058722, mailed Mar. 11, 2011.

International Search Report and Written Opinion issued in PCT/US2010/058982, mailed Mar. 3, 2011, 12 pages.

\* cited by examiner

ELECTRODE SURFACE MODIFICATION FOR IMPARTING CURRENT DENSITY DIRECTIONALITY IN LEAD ELECTRODES

CROSS-REFERENCE TO RELATED APPLICATION

This application claims priority under 35 U.S.C. §119 to U.S. Provisional Application No. 61/291,157, filed Dec. 30, 2009, entitled "Electrode Surface Modification For Imparting Current Density Directionality In Lead Electrodes," which is incorporated herein by reference in its entirety for all purposes.

TECHNICAL FIELD

The present invention relates generally to implantable medical devices. More specifically, the present invention relates to implantable medical leads with electrode surface modification for imparting current density directionality within lead electrodes.

BACKGROUND

Various types of medical electrical leads for use in cardiac rhythm management (CRM) and neurostimulation applications are known. In CRM applications, for example, such leads are frequently delivered intravascularly to an implantation location on or within a patient's heart, typically under the aid of fluoroscopy. Once implanted, the lead is coupled to a pulse generator or other implantable device for sensing cardiac electrical activity, delivering therapeutic stimuli, and/or for performing some other desired function within the body. Such leads often include a distal, conductor section which contacts the heart tissue, and a proximal, terminal section which is connected to a pulse generator. The distal section of the lead can include a number of ring-shaped electrodes that supply electrical currents to adjacent heart tissue for pacing the heart and/or for sensing heart function. The electrodes are typically attached to a conductor cable or coil within the interior of the lead via a welded, crimped, and/or staked connection joint.

In some lead designs, the distal section of the lead may have a pre-biased shape that is used to secure the lead within the body. In certain lead configurations, for example, the implantable lead can have a helical or S-shaped distal section that serves to secure the lead to the walls of a vein or artery. When implanted within the body, the electrodes may have an inactive portion that does not contact adjacent target tissue, but which affects the current density around the surface of the electrode. Furthermore, in some cases the inactive portion of the electrode can direct current toward an undesired stimulation site such as the phrenic nerve in CRM applications. In some cases, the inactive portion of the electrode not in contact with the target tissue can decrease the amplitude of the current density at the active region of the electrode, reducing the overall efficiency of the electrode in providing electrical stimulus and/or to sense cardiac electrical activity. For ring-type electrodes having a uniform wall thickness throughout, for example, the electrodes often include one or more inactive portions that are not in contact with the adjacent target body tissue, but which affect the magnitude and directionality of the current density.

SUMMARY

The present invention relates generally to implantable medical leads having modified electrode surfaces for imparting current density directionality within lead electrodes.

In Example 1, an implantable medical lead in accordance with an illustrative embodiment includes a lead body having a proximal section and a distal section, and at least one electrode disposed on the distal section of the lead body, the at least one electrode including an active electrode portion and an inactive electrode portion, the active electrode portion configured to contact a body vessel, the inactive electrode portion including a plurality of surface features configured to impart a current density directionality towards the active electrode portion.

In Example 2, the implantable medical lead according to Example 1, wherein the surface features include a plurality of ridges.

In Example 3, the implantable medical lead according to Example 2, wherein a height of each ridge is between about 0.001 inches to 0.005 inches.

In Example 4, the implantable medical device according to any of Examples 2-3, wherein a distance between each adjacent ridge is between about 0.003 inches to 0.007 inches.

In Example 5, the implantable medical lead according to any of Examples 1-4, wherein the at least one electrode comprises a ring-shaped electrode.

In Example 6, the implantable medical lead according to any of Examples 1-5, wherein the ridges extend lengthwise about at least a portion of a circumference of the electrode.

In Example 7, the implantable medical lead according to any of Examples 1-6, wherein the electrode includes a first semi-circular section and a second semi-circular section, the first and second semi-circular sections separated from each other via a centerline of the electrode.

In Example 8, the implantable medical lead according to Example 7, wherein the ridges extend lengthwise about a circumference of the first semi-circular section.

In Example 9, the implantable medical lead according to any Examples 1-8, wherein the surface features include a first number of surface features disposed on an exterior surface of the electrode and a second number of surface features disposed on an interior surface of the electrode.

In Example 10, the implantable medical lead according to any of Examples 1-9, wherein the at least one electrode further includes a layer of insulation disposed on the inactive electrode portion of the electrode.

In Example 11, the implantable medical lead according to any of Examples 1-10, wherein the surface features includes a plurality of bumps.

In Example 12, the implantable medical lead according to any of Examples 1-4 and 6-11, wherein the at least one electrode comprises a semi-annular shaped electrode.

In Example 13, an implantable medical lead comprises a lead body having a proximal section and a distal section, the distal section of the lead body having a pre-biased shaped configured to secure the lead to an inner wall of a blood vessel and at least one annular-shaped electrode. At least one electrode includes a conductor body having a first, active electrode section configured to contact the inner wall and a second, inactive electrode section. The second electrode section includes a plurality of ridges configured to impart a current density directionality towards the first electrode section.

In Example 14, a method for imparting current density directionality within an electrode of an implantable lead comprises identifying an active electrode portion and an inactive electrode portion of the electrode, selectively treating the inactive portion of the electrode to form a plurality of surface features on the electrode, the plurality of surface features configured to impart a current density directionality within the electrode towards the active electrode portion.

In Example 15, the method according to Example 14, wherein selectively treating the inactive electrode portion of the electrode includes selectively forming a plurality of ridges on the electrode.

In Example 16, the method according to Example 15, wherein the ridges extend lengthwise perpendicular to a longitudinal axis of the electrode.

In Example 17, the method according to Example 15, wherein the ridges extend lengthwise parallel to a longitudinal axis of the electrode.

In Example 18, the method according to Example 15, wherein the ridges extending lengthwise at an angle relative to a longitudinal axis of the electrode.

In Example 19, the method according to Example 14, wherein selectively treating the inactive electrode portion of the electrode includes selectively forming a plurality of bumps on the electrode.

In Example 20, the method according to any of Examples 1-19, wherein selectively treating the inactive electrode portion of the electrode includes selectively treating an exterior surface of the electrode to form a plurality of surface features on the exterior surface of the electrode, and selectively treating an interior surface of the electrode to form a plurality of surface features on the interior surface of the electrode.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
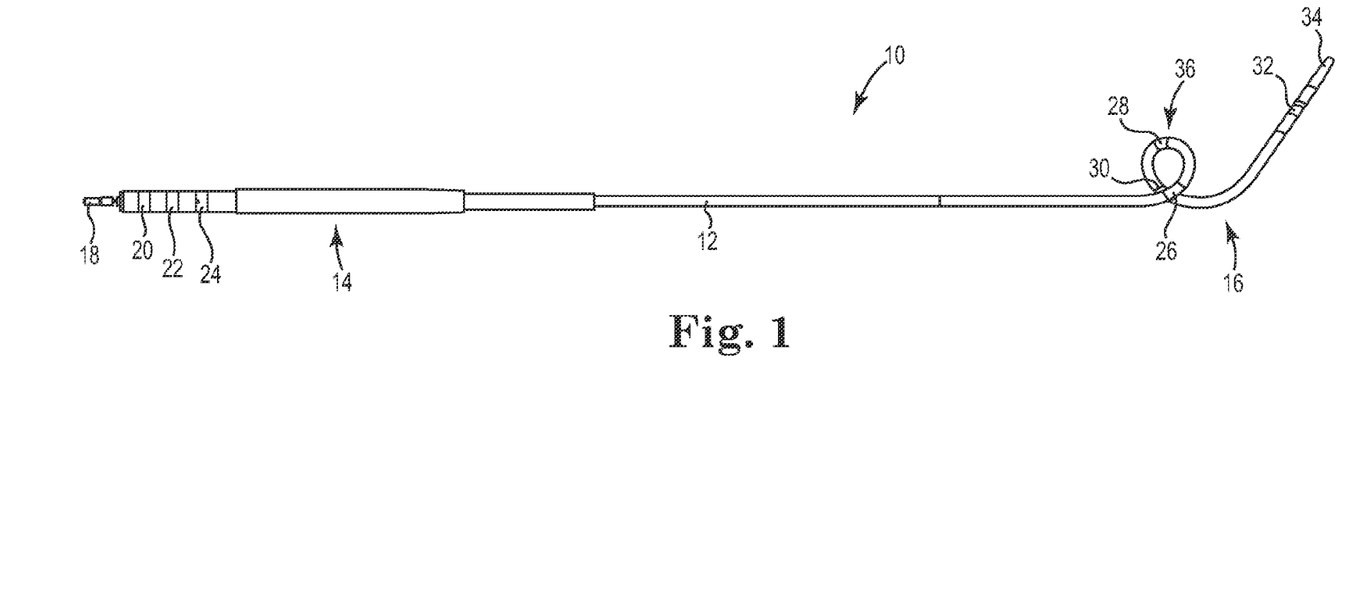
FIG. 1 is a perspective view showing an implantable lead configured for providing electrical stimulus therapy and/or for sensing electrical activity within a patient's body.

FIG. 1 is a perspective view showing an implantable lead 10 configured for providing electrical stimulus therapy and/or for sensing electrical activity within a patient's body. The implantable lead 10, illustratively a quadripolar cardiac lead, includes a lead body 12 having a proximal section 14 and a distal section 16. The proximal section 14 of the implantable lead 10 includes a terminal pin 18 and a number of terminal ring contacts 20,22,24 that connect to a pulse generator such as a pacemaker, implantable cardioverter defibrillator (ICD), cardiac resynchronization therapy (CRT) device, or the like.

The distal section 16 of the implantable lead 10 includes a number of electrodes each coupled to a corresponding cable conductor or coil conductor within the interior of the lead 10. In the embodiment of FIG. 1, for example, the implantable lead 10 includes three electrodes 26,28,30 each electrically connected to a corresponding terminal contact 20,22,24 on the lead 10. Another electrode 32 on the implantable lead 10 is electrically coupled to the terminal pin 18, and is located at a distal tip section 34 of the lead 10 configured to engage the vessel wall. During operation, a pulse generator supplies electrical pulses to the electrodes 26,28,30,32 for pacing the heart and/or for sensing cardiac electrical activity.

In certain embodiments, the distal section 16 has a pre-biased shape that engages the inner diameter of a vessel wall to secure the lead 10 within a blood vessel and/or to promote electrode contact with the target tissue. As shown in FIG. 1, for example, the distal section 16 includes a pre-biased helical section 36 that can be used to secure the lead 10 to the inner wall of a coronary vein, pulmonary artery, or other such vessel. Other configurations are also possible. In one alternative embodiment, for example, the distal section 16 of the implantable lead 10 can include an S-shaped or J-shaped configuration for insertion within a blood vessel or within a chamber of the heart. The shape imparted to the distal section 36 will typically vary based on the anatomy at the implantation location and the delivery mechanism. As discussed further below, the orientation of the electrodes 26,28,30,32 can also vary depending on the particular shape imparted to the implantable lead 10.

Figure 2:
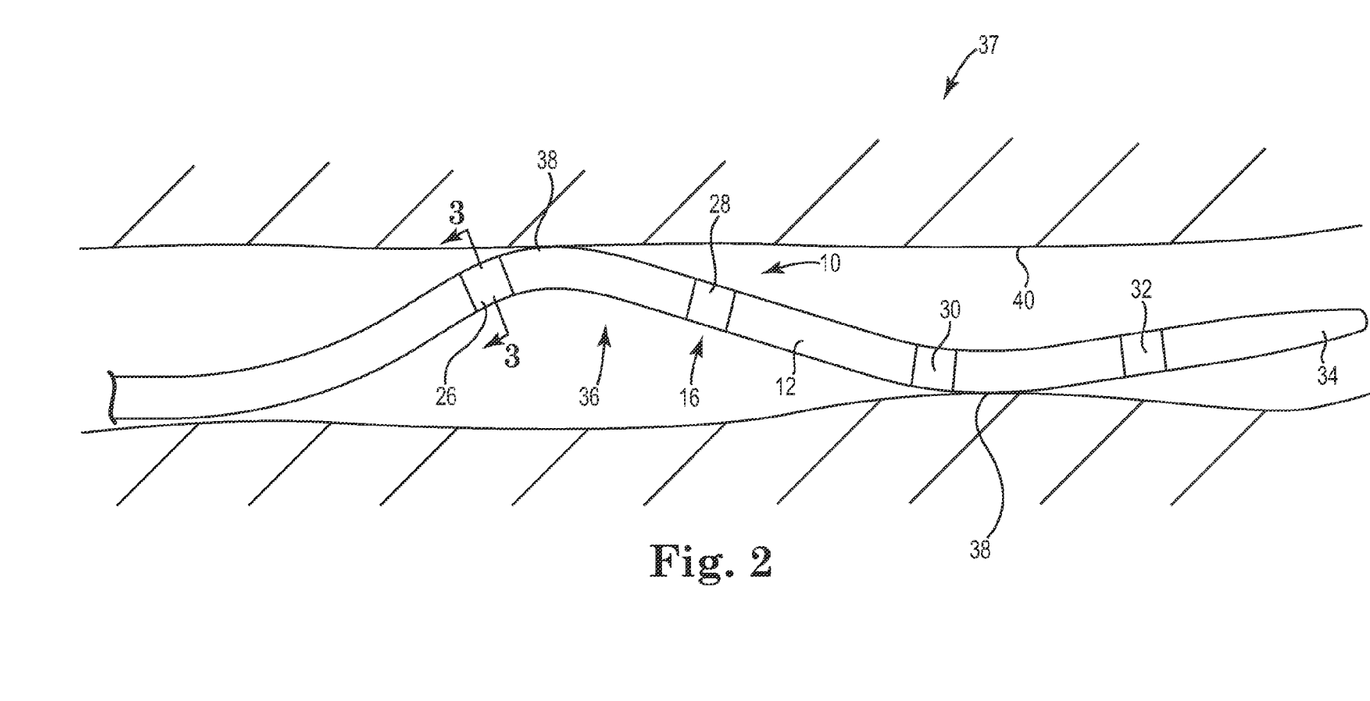
FIG. 2 is a schematic view showing the implantable lead of FIG. 1 inserted at a target region within a blood vessel.

FIG. 2 is a schematic view showing the implantable lead 10 of FIG. 1 inserted at a target region within a blood vessel such as a coronary vein 37. As further shown in FIG. 2, when inserted into the vein 37, an outwardly-facing portion 38 of the helical section 36 is configured to engage the inner wall 40 of the vein 37, which in addition to the distal tip section 34, frictionally secures the lead 10 in place within the vein 37. In some embodiments, the inwardly-directed force from the inner wall 40 of the vein 37 opposes the outwardly-directed force from the helical section 36, which further serves to frictionally secure the implantable lead 10 within the vein 37. In some embodiments, each of the electrodes 26,28,30,32 can be positioned on the lead 10 so as to increase, and in some embodiments optimize, the likelihood of target tissue contact.

Figure 3:
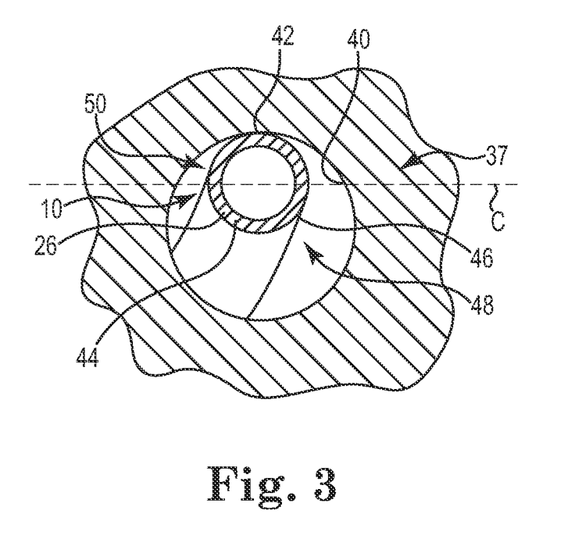
FIG. 3 is a transverse cross-sectional view of the electrode across line 3-3 in FIG. 2.

As further shown in FIG. 2, and in some embodiments, the electrodes 26,28,30,32 each comprise ring-type electrodes spaced apart from each other along the length of the lead body 12 for pacing and/or sensing at various locations along the length of the vein 37. The electrodes 26,28,30,32 are each fabricated from an electrically conductive material such as platinum, palladium, titanium, gold, or MP35N. Due to the helical shape of the implantable lead 10 at section 36, only a portion of each of the electrodes 26,28,30,32 contacts the inner wall 40 of the vein 37. As further shown across line 3-3 in FIG. 3, for example, only an active, outer facing portion 42 of the electrode 26 contacts the inner wall 40 of the vein 37. An inwardly facing, inactive portion 44 of the electrode 26 oriented towards the interior of the vein 37, in turn, does not contact the inner wall 40.

On implantable leads having a pre-biased shape, the location(s) where the lead contacts the vessel wall can often be reliably predicted. In such case, and in some embodiments, the orientation of the active, outer facing portion 42 and inactive, inwardly facing portion 44 of the electrodes 26,28, 30,32 may vary depending on the shape of the lead and the surrounding anatomy. In a helical-shaped configuration such as that shown in FIG. 2, for example, the active electrode portion of each of the three electrodes 26,28,30 on the helical section 36 can be offset circumferentially at different angles from each other based on the path of the helix. In one embodiment, for example, each of the electrodes 26,28,30 can each be circumferentially offset from each other at an angle of between 30° to 60° around the lead body 12. Other configurations are also possible.

The current density within each of the electrodes 26,28,30, 32 can be defined generally as a vector representing the electrical current per unit area of cross section. The directional aspect of the current density vector is based on a number of factors, including the geometry, surface characteristics, and construction of the electrodes 26,28,30,32. During pacing and/or sensing, the current density within the electrode 26,28, 30,32 affects the amount of current that is delivered to the adjacent body tissue.

Figure 4:
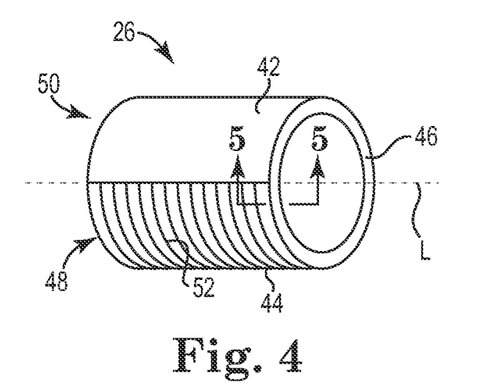
FIG. 4 is a perspective view showing one of the electrodes of FIG. 1 in greater detail.

FIG. 4 is a perspective view showing one of the electrodes 26 in greater detail. As can be further seen in conjunction with FIGS. 3-4, the electrode 26 comprises an annular-shaped conductor body 46 having a first semi-circular section 48 and a second semi-circular section 50. The first and second sections 48,50 are separated from each other via an imaginary centerline C, which extends across the width of the electrode 26 perpendicular to its longitudinal axis L. In the embodiment shown, the first section 48 of the conductor body 46 includes a number of ridges 52 circumferentially disposed on the inactive portion 44 of the electrode 26. In certain embodiments, and as further shown in FIG. 4, the ridges 52 are extend lengthwise in a direction perpendicular to the longitudinal axis L. The ridges 52 can be formed, for example, by selectively modifying the exterior surface of the first section 48. In one embodiment, the ridges 52 can be formed by laser etching portions of the exterior surface of the first section 48 using a laser source. The second section 50 of the electrode 26 including the active, outwardly facing 42 surface, in turn, does not contain any ridges 52.

In the embodiment shown in FIG. 4, the ridges 52 extend about only a portion of the circumference of the electrode 26. In one embodiment, for example, the ridges 52 extend lengthwise about approximately ½ of the circumference of the electrode 26. In other embodiments, the ridges 52 may extend about a greater or lesser portion of the circumference of the electrode 26. In use, the presence of the ridges 52 on the inactive portion 44 of the electrode 26 serves to decrease the current density on the first section 48 of the electrode 26 as compared to the second section 50. This localized decrease in current density imparts a directionality towards the active portion 42 of the electrode 26 that contacts the myocardium. This directionality towards the myocardium and away from other regions in the vein 37 facilitates increased charge transfer between the active portion 42 of the electrode 26 and adjacent body tissue, thereby increasing the ability of the electrode 26 to pace and sense while also reducing extracardiac stimulation of other regions of the body.

Figure 5:
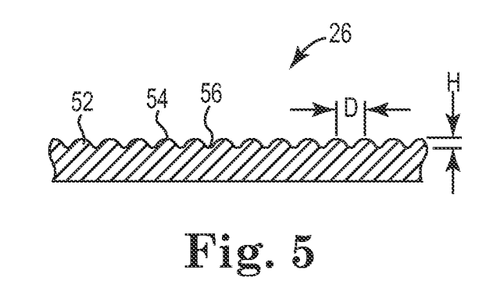
FIG. 5 is a partial cross-sectional view along line 5-5 in FIG. 4.

FIG. 5 is a partial cross-sectional view of the electrode 26 along line 5-5 in FIG. 4. As further shown in FIG. 5, and in some embodiments, each of the ridges 52 have a rounded shape with a peak 54 and a valley 56. In some embodiments, the height H of each of the ridges 52 as measured from the peak 54 to the valley 56 is between about 0.001 inches to about 0.005 inches. In some embodiments, the spacing or distance D between each adjacent peak 54 is about 0.003 inches to about 0.007 inches. In one embodiment, the peak to valley height H of each ridge 52 is 0.001 inch with a 0.005 inch spacing D between adjacent peaks 54. The height H and/or spacing D between adjacent peaks 54 may vary, however, depending on the total length of the electrode 26, the thickness of the electrode 26, the surface area of the electrode 26, as well as other factors. In some embodiments, the depth of the valleys 56 may approach the wall thickness of the electrode 26, creating slots within the electrode 26.

Figure 6:
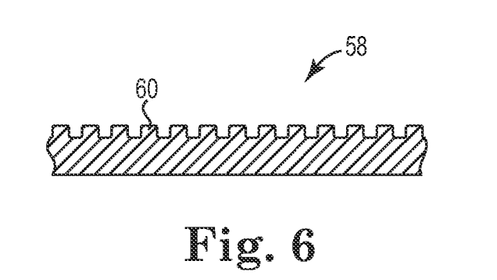
FIG. 6 is a partial cross-sectional view showing an electrode in accordance with another illustrative embodiment including square-shaped ridges.

FIG. 6 is a partial cross-sectional view showing an electrode 58 in accordance with another illustrative embodiment. As shown in FIG. 6, the electrode 58 includes a number of square-shaped ridges 60 that extend lengthwise about a portion of the circumference of the electrode 60 perpendicular its longitudinal axis. The ridges 60 can include rounded and filleted edges, and may have a height and spacing similar to the rounded ridges 52 discussed above. In use, the presence of the ridges 60 serves to decrease the current density on an inactive portion of the electrode 58, imparting a current density directionality towards an active portion of the electrode 58 that contacts the body tissue.

Figure 7:
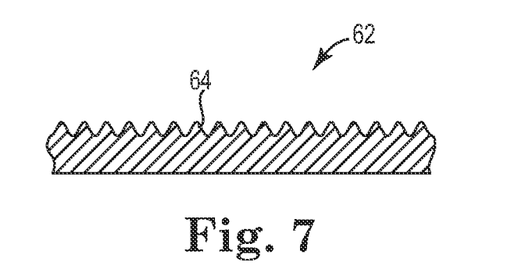
FIG. 7 is a partial cross-sectional view showing an electrode in accordance with another illustrative embodiment including V-shaped ridges.

FIG. 7 is a partial cross-sectional view showing an electrode 62 in accordance with another illustrative embodiment. As shown in FIG. 7, the electrode 62 includes a number of V-shaped ridges 64 that extend lengthwise about a portion of the circumference of the electrode 62 perpendicular to its longitudinal axis. The ridges 64 can include rounded and filleted edges, and may have a height and spacing similar to the ridges 52 discussed above. In use, the presence of the ridges 64 serves to decrease the current density on an inactive portion of the electrode 62, imparting a current density directionality towards an active portion of the electrode 58 that contacts the body tissue.

Figure 8:
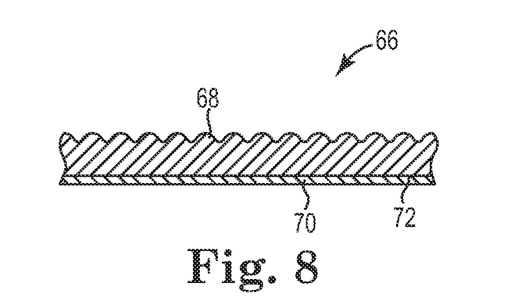
FIG. 8 is a partial cross-sectional view showing an electrode in accordance with another illustrative embodiment including a layer of insulation.

FIG. 8 is a partial cross-sectional view showing an electrode 66 in accordance with another illustrative embodiment. The electrode 66 is similar to the electrode 26 of FIG. 4, including a number of rounded ridges 68 that extend lengthwise about a portion of the circumference of the electrode 66. In the embodiment of FIG. 8, the electrode 66 further includes a layer of insulation 70 disposed on the inner wall 72 of the electrode 66. In addition to the ridges 68 on the inactive portions of the electrode 66, the layer of insulation 70 further alters the current density directionality within the electrode 66. In those embodiments in which the electrode 66 is configured to pace and/or sense the myocardium, for example, the presence of the ridges 68 and the layer of insulation 70 increases the current density on the active portion of the electrode 66 adjacent to the myocardium while decreasing the current density in other directions that may lead to undesired extracardiac stimulation of other anatomy (e.g., the pericardium or phrenic nerve).

Figure 9:
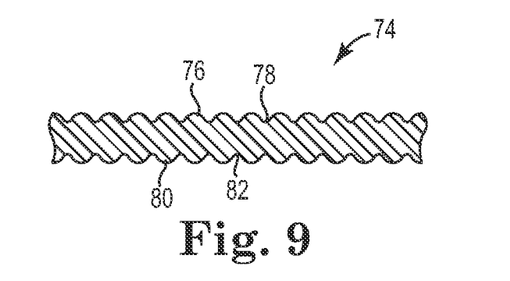
FIG. 9 is a partial cross-sectional view showing an electrode in accordance with another illustrative embodiment including ridges on multiple sides of the electrode.

FIG. 9 is a partial cross-sectional view showing an electrode 74 in accordance with another illustrative embodiment including ridges on both sides of the electrode 74. As shown in FIG. 9, the electrode 74 includes a first number of ridges 76 on an exterior portion 78 of the electrode 74 and a second number of ridges 80 on an interior portion 82 of the electrode 74. The ridges 76,80 can be configured similar to the ridges 52 discussed above, and extend lengthwise about a portion of the circumference of the electrode 74 perpendicular to its longitudinal axis. In some embodiments, the ridges 76 on the exterior section 78 of the electrode 74 are disposed on only an inactive portion of the electrode 74 whereas the ridges 80 on the interior section 82 of the electrode 74 are disposed on the entire inner section 82 of the electrode 74. In other embodiments, both sets of ridges 76,80 are disposed on only a portion of each corresponding electrode section 78,82.

The shape and/or configuration of the electrodes can differ from the electrodes 26,62,66,74 shown in FIGS. 4-9. In some embodiments, the distribution of the conductor mass and/or the surface geometry of the electrodes can also be configured so as to impart a current density directionality at or near the active portion of the electrode where the electrode contacts adjacent body tissue. An example of an implantable medical lead having an asymmetrically distributed conductor mass and/or surface geometry is described in co-pending U.S. Application Publication No. 2011/0160822, entitled "Implantable Lead Electrode With Asymmetrically Distributed Current Density and Methods For Imparting Current Density Directionality In Lead Electrodes," which is incorporated herein by reference in its entirety for all purposes.

Figure 10:
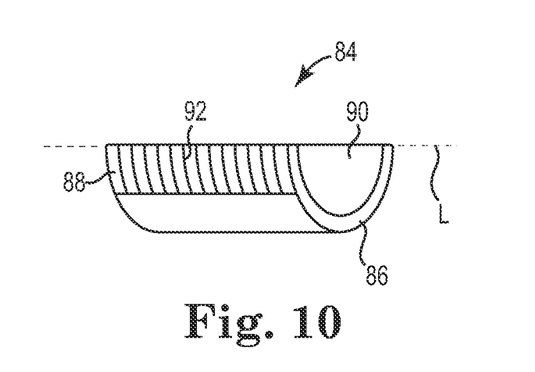
FIG. 10 is a perspective view showing an electrode in accordance with another illustrative embodiment.

FIG. 10 is a perspective view showing an electrode 84 in accordance with another illustrative embodiment. As shown in FIG. 10, the electrode 84 comprises a semi-annular shaped conductor body 86 having an exterior section 88 and an interior section 90. The exterior section 88 is exposed on the exterior of the lead, and is configured to contact body tissue on the inner wall 40 of the vein 37. The interior section 90 of the electrode 84, in turn, faces the interior of the lead, and does not contact the inner wall 40.

A number of ridges 92 on a portion of the exterior section 88 extend lengthwise in a direction perpendicular to a longitudinal axis L of the electrode 84. The ridges 92 can extend about only an inactive portion of the exterior surface 88. An active portion of the electrode 84 adapted to contact myocardial tissue, in turn, does not include the ridges 92. In use, the presence of the ridges 92 on the inactive portion of the electrode 84 serves to decrease the localized current density on the inactive portion. This localized decrease in current density imparts a directionality towards the active portion of the electrode 84 that contacts the body tissue.

Figure 11:
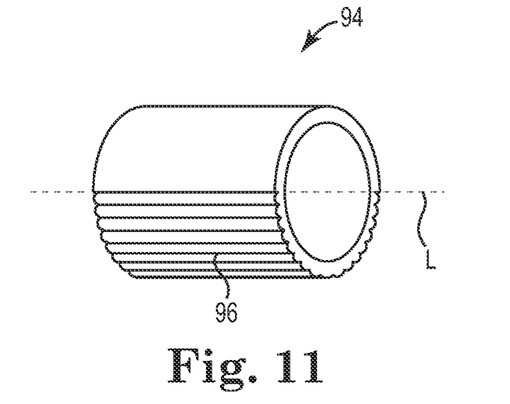
FIG. 11 is a perspective view showing an electrode in accordance with another illustrative embodiment.

The orientation of the ridges 92 can also be altered to further impart a current density directionality within the electrode. In one alternative embodiment shown in FIG. 11, for example, an electrode 94 can include a number of ridges 96 that extend lengthwise in a direction parallel to the longitudinal axis L of the electrode 94. In other embodiments, the ridges 96 extend lengthwise at an angle relative to the longitudinal axis L. In one such embodiment, for example, the ridges 96 can be oriented at 15°, 30°, 45°, 60°, 75°, or some other desired angle relative to the longitudinal axis L. The ridges can be rounded, squared, V-shaped, or some other desired shape.

Figure 12:
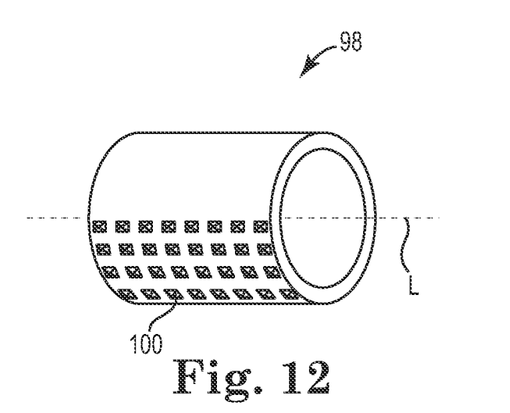
FIG. 12 is a perspective view showing an electrode in accordance with another illustrative embodiment.

FIG. 12 is a perspective view showing an electrode 98 in accordance with another illustrative embodiment. As shown in FIG. 12, and in some embodiments, the surface of the electrode 98 can be modified to form other desired shapes on one or more inactive portions of the electrode 98. In the embodiment shown, for example, a number of pyramidal-shaped bumps 100 can be formed by selectively modifying the exterior surface of the electrode 98 (e.g., using a laser etching process). As with ridges, the bumps 100 are configured to decrease the current density on an inactive portion of the electrode, imparting a current density directionality towards an active portion of the electrode 98. Other suitable shapes can also be imparted to the inactive portions of the electrode 98.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. An implantable medical lead, comprising:
a lead body having a proximal section and a distal section; and
at least one electrode fabricated from an electrically conductive material and disposed on the distal section of the lead body, the at least one electrode including an active electrode portion and an inactive electrode portion, the active electrode portion configured to contact target tissue, the inactive electrode portion including a plurality of surface features formed in the electrically conductive material, the plurality of surface features configured to impart a current density directionality towards the active electrode portion.

2. The implantable medical lead of claim 1, wherein the surface features include a plurality of ridges.

3. The implantable medical lead of claim 2, wherein a height of each ridge is between about 0.001 inches to 0.005 inches.

4. The implantable medical device of claim 3, wherein a distance between each adjacent ridge is between about 0.003 inches to 0.007 inches.

5. The implantable medical lead of claim 2, wherein the at least one electrode comprises a ring-shaped electrode.

6. The implantable medical lead of claim 5, wherein the ridges extend lengthwise about at least a portion of a circumference of the electrode.

7. The implantable medical lead of claim 5, wherein the electrode includes a first semi-circular section and a second semi-circular section, the first and second semi-circular sections separated from each other via a centerline of the electrode.

8. The implantable medical lead of claim 5, wherein the ridges extend lengthwise about a circumference of the first semi-circular section.

9. The implantable medical lead of claim 1, wherein the surface features include a first number of surface features disposed on an exterior surface of the electrode and a second number of surface features disposed on an interior surface of the electrode.

10. The implantable medical lead of claim 1, wherein the at least one electrode further includes a layer of insulation disposed on the inactive electrode portion of the electrode.

11. The implantable medical lead of claim 1, wherein the surface features includes a plurality of bumps.

12. The implantable medical lead of claim 1, wherein the at least one electrode comprises a semi-annular shaped electrode.

13. An implantable medical lead, comprising:
a lead body having a proximal section and a distal section, the distal section of the lead body having a pre-biased shaped configured to secure the lead to an inner wall of a blood vessel; and at least one annular-shaped electrode disposed on the distal section of the lead body, the at least one electrode including a conductor body having a first, active electrode section configured to contact the inner wall and a second, inactive electrode section, the second electrode section including a plurality of ridges formed from electrically conductive material of the electrode, the plurality of ridges configured to impart a current density directionality towards the first electrode section, the first active electrode section oriented on the lead body to be outward facing to contact a target tissue due to the pre-biased shaped of the lead body and the second inactive electrode section orientated on the lead body to be inward facing to not contact the target tissue due to the pre-biased shape of the lead body.

14. A method for imparting current density directionality within an electrode of an implantable lead, the electrode fabricated from electrically conductive material, the method comprising:

identifying an active electrode portion and an inactive electrode portion of the electrode; and selectively treating the inactive portion of the electrode to form a plurality of surface features from the electrically conductive material on the electrode, the plurality of surface features configured to impart a current density directionality within the electrode towards the active electrode portion.

15. The method of claim 14, wherein selectively treating the inactive electrode portion of the electrode includes selectively forming a plurality of ridges on the electrode.

16. The method of claim 15, wherein the ridges are circumferentially disposed about the inactive portion of the electrode and extend lengthwise perpendicular to a longitudinal axis of the electrode.

17. The method of claim 15, wherein the ridges extend lengthwise parallel to a longitudinal axis of the electrode.

18. The method of claim 15, wherein the ridges extending lengthwise at an angle relative to a longitudinal axis of the electrode.

19. The method of claim 14, wherein selectively treating the inactive electrode portion of the electrode includes selectively forming a plurality of bumps on the electrode.

20. The method of claim 14, wherein selectively treating the inactive electrode portion of the electrode includes:

selectively treating an exterior surface of the electrode to form a plurality of surface features on the exterior surface of the electrode; and selectively treating an interior surface of the electrode to form a plurality of surface features on the interior surface of the electrode.

* * * * *